United States Patent
Komai et al.

[11] Patent Number: 6,034,120
[45] Date of Patent: Mar. 7, 2000

[54] INSECT ANTIFEEDANT FOR AGRICULTURE

[75] Inventors: Koichiro Komai, Kyoto; Masanori Morimoto, Nara; Toyoshige Morita, Osaka, all of Japan

[73] Assignee: Morita Kaguku Kogyo Co., Ltd., Osaka, Japan

[21] Appl. No.: 09/028,879

[22] Filed: Feb. 24, 1998

[30] Foreign Application Priority Data

Aug. 29, 1997 [JP] Japan ..................................... 9-234220

[51] Int. Cl.$^7$ ........................... A61K 31/35; A61K 31/34; C07D 493/00; C07D 307/00; C07D 317/70
[52] U.S. Cl. ........................... 514/455; 514/454; 514/468; 514/469; 514/470; 514/453; 549/387; 549/385; 549/469; 549/433
[58] Field of Search ..................................... 549/387, 469, 549/433; 514/470, 469, 454, 455, 468

[56] References Cited

PUBLICATIONS

Kokate C. K.; (Napralert AN 92:81789, abstract of 4th Asian symp Med Plants species, Bangkok, Thailand, Sep. 15–19, 1980, p. 154.
Nayar S. L. ( Bull. Natl Inst. Sci India (1955) (4) p. 137–145).
Kokate et al. (Napralert AN 92:56673, abstract of Indian J. Pharm. Sci. (1982), 44 p. 14pp–).
Chesney et al., (Econ. Bot. (1985), 39 (1), p. 74–86).

*Primary Examiner*—Jose' G. Dees
*Assistant Examiner*—Sabiha N. Qazi

[57] ABSTRACT

The present invention provides an antifeedant and a contact insecticide using the components contained in Cyperaceae species. In particular, the present invention provides an insect antifeedant and a contact insecticide comprising as an active ingredient at least one compound selected from the group consisting of scabequinone, remirol, cyperaquinone and the derivatives thereof.

1 Claim, No Drawings

INSECT ANTIFEEDANT FOR AGRICULTURE

BACKGROUND OF THE INVENTION

1. Field of the Invention

The present invention relates to an antifeedant and a contact insecticide comprising the components contained in Cyperaceae species.

2. Description of the Prior Art

In agriculture, plant damage due to insects is unavoidable. In the old days, pyrethroid was used as a natural insecticide. Nowadays, pyrethrin, which is a component of pyrethroid, is synthesized and utilized as an insecticide. In addition to these, nicotine sulfate and machine oil are insecticides obtained from natural substances. However, no effective insecticides have been obtained from natural substances, except for pyrethroid and its component, pyrethrin.

On the other hand, the use of powerful synthesized pesticides (a herbicide, an insecticide, an anti-microbial agent) tend to cause the appearance of resistant organisms. *Erigeron annuus* PERS and the like, which are resistant to paraquat are ones which acquired the resistance at an early stage. Concerning insects, especially among those having a short generation time, this phenomenon is confirmed in the early stages. Because of the appearance of these organisms having resistance, it becomes necessary to develop new treatment agents having novel functions. It is also essential for those who raise crops to control harmful insects with agents, and the use of powerful pesticides for that purpose results in the disturbance of the ecosystem of a treated area. For example, the use of insecticides against one harmful insect, can cause the explosive breeding of another harmful insect.

A study directed to the use of antifeedant has been conducted in order to protect the plants from the harmful insects. Particularly, a study directed to juglon, which is contained in a walnut, as a natural antifeedant has been conducted. However, juglon has a strong anti-breeding effect on the plants and therefore it has not been put to practical use.

We have carried out an intensive study directed to the development of a safe, natural antifeedant, insecticide and pesticide which contains no halogen, and which does not cause development of resistance in harmful insects and which does not disturb the ecosystem and as a result, the present invention was accomplished.

A method for protecting the plants from the harmful insects by preventing them from eating the plants was studied, and we found that scabequinone, remirol, cyperaquinone and the derivatives thereof, which are present in Cyperaceae species, are antifeedants. The present invention is based on the findings.

SUMMARY OF THE INVENTION

The present invention provides an insect antifeedant or a contact insecticide which comprises as an active ingredient at least one compound selected from the group consisting of scabequinone, remirol, cyperaquinone and derivatives thereof. The present invention also discloses that these active ingredients are present in extracts of Cyperaceae species.

The repellant of the present invention barely causes any disturbance to the ecosystem due to a sudden change in the number of insects and the like, and it can move the harmful insects (pests) from an area which it is desirable to protect.

It is also expected that the appearance of resistant species will be retarded.

Furthermore, these compounds not only repel the harmful insects from the plants, but also have an insecticidal effect on consumption similar to conventional insecticides. It was also found that they were effective as insecticides in the case where the harmful insects come into contact these compounds when they are sprayed on plants. By having an insecticidal effect on contact, the insecticide of the present invention can be effective in the case where the harmful insects eat the plants, while avoiding indiscriminate insecticide effect and conserving the ecosystem.

Namely, although the present invention has an insecticidal effect, it is characterized by prioritizing an antifeeding effect such that the harmful insects do not eat the plants, and by acting as an effective insecticide if the harmful insects do eat the plants.

Therefore, the first aspect of present invention is to provide an insect antifeedant which comprises as an active ingredient at least one compound selected from the group of scabequinone, remirol, cyperaquinone and the derivatives thereof.

The second aspect of the present invention is to provide a contact insecticide comprising as an active ingredient at least one compound selected from the group consisting of scabequinone, remirol, cyperaquinone and the derivatives thereof.

The active ingredient may be an extract of Cyperaceae species plants containing at least one compound selected from the group consisting of scabequinone, remirol, cyperaquinone and the derivatives thereof.

The antifeedant or the contact insecticide of the invention may be applied to or contact insects in a field of crop plants in to provide effective amount of at least one compound selected from the group consisting of scabequinone, remirol, cyperaquinone and the derivatives thereof or an extract of Cyperaceae species plants containing it.

DETAILED DESCRIPTION OF THE PREFERRED EMBODIMENTS

Scabequinone, remirol and cyperaquinone are the compounds having the following chemical formula:

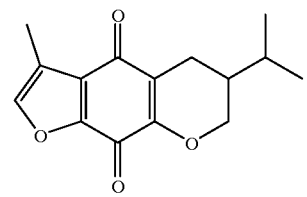

Scabequinone

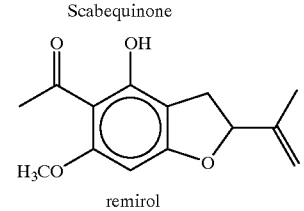

remirol

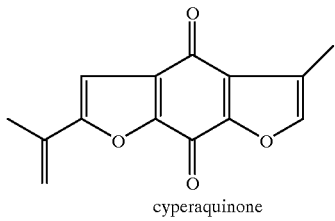
cyperaquinone

Examples of the derivative of scabequinone include dihydroscabequinone, 2-isopentyl-3-methoxy-4,5-franobenzoquinone, 2-isopenetyl-3-methoxy-4,5-franobenzoquinone and the like.

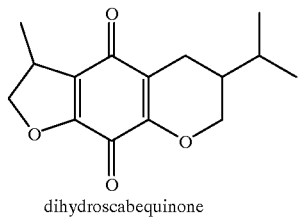
dihydroscabequinone

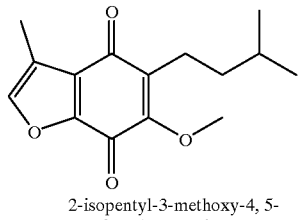
2-isopentyl-3-methoxy-4, 5-franobenzoquinone

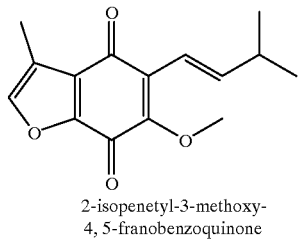
2-isopenetyl-3-methoxy-4, 5-franobenzoquinone

Examples of the derivatives of remirol include 2-isopropenyl-4,6-methoxycoumaran, methylremirol and its racemic modification, epoxyremirol, acetylremirol, $C_{1-6}$alkylsubstituted-remirol and the like.

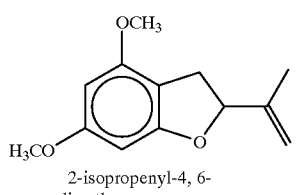
2-isopropenyl-4, 6-dimethoxycoumaran

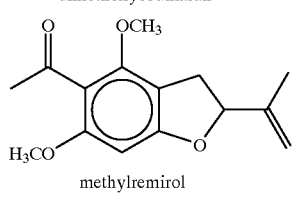
methylremirol

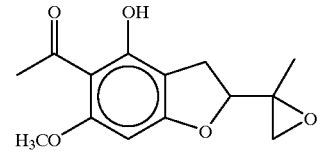
epoxyremirol

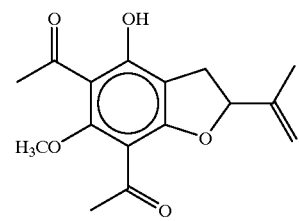
acetylremirol

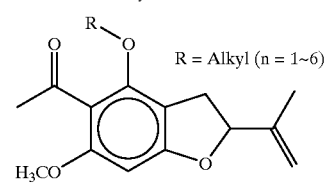
$C_{1-6}$alkylsubstituted-remirol

R = Alkyl (n = 1~6)

Typical examples of Cyperaceae species include *Cyperus distans, C. nipponicus, C. stoloniferus, C. pulcherrimus, C. iria, C. javanicus, C. cyperinus, C. nutans, C. trialatus, C. diffusus, C. serotinus, C. pilosus, C. orthostachyus, C. monophyllus, C. haspan, C. brevifolius, C. odoratus, C. compressus, C. sanquiolentus* and the like.

In the *C. nipponicus* collected in the Kinki region of Japan, remirol and cyperaquinone are contained in a great amount. In the *C. distans* from the torrid zone, scabequinone is contained in a great amount.

Extraction of Cyperaceae species is conducted by using solvents such as hexane, ethanol, isopropylalcohol or acetone.

Scabequinone is obtained by extracting roots or bulbs of *Cyperus distans* with organic solvents such as hexane or alcohol, followed by concentration; or is obtained by concentrating an extract, then, adding an organic solvent in which scabequinone is insoluble. Remirol is obtained by extracting roots or bulbs of *Cyperus nipponicus* with hexane and distilling off hexane, adding ethanol to the residue to prepare an ethanol solution, removing a wax component, concentrating the residue under reduced pressure, adding hexane to the residue to prepare a hexane solution, filtering the precipitated cyperaquinone, and fractionating the filtered portion by column chromatography on silica gel (Wakogel C-300) using a developer (hexane:ethyl acetate=10:1). Based on the respective compounds, each derivative can be obtained using conventional synthesizing methods.

Separation of Scabequinone

In order to confirm an antifeeding effect, 100 g of bulbs of Cyperaceae *Cyperus distans* were ground and soaked in 5-fold hexane for 3 days. Thereafter, the mixture was filtered, and the filtrate was concentrated under reduced pressure to obtain 40 mg of yellow crystals. The melting point was 105–110° C. The analyzed values of the crystals are as follows. scabequinone: yellow needle crystals m.p. 105–110

UV(MeOH) λmax(nm) 430, 322, 268, 220

IR(KBr) vmax $cm^{-1}$ 3128, 2962, 2875, 1683, 1647, 1610, 1577 1523, 1467, 1355, 1232, 1120, 1043, 1001, 916, 744

LR-MS m/z (rel.int.%) 260(M⁺)(91.8), 245(39.8), 217(100), 204(16.9), 189(36.4), 163(27.7), 109(16.4), 82(18.3), 70(32.9), 56(22.1)

$^{1}$H-NMR ppm (J=Hz) 1.07(6H d, J=6.5), 1.55–1.75(2H, m), 2.11(1H d.d. J=18.0, 10.0), 2.28(3H d. J=1.0), 2.68(1H d.d.d. J=18.0, 5.0, 2.5), 3.79(1H t. J=10.0), 4.48(1H d.t. J=10.0, 2.5), 7.46(1H d. J=1.0)

$^{13}$C-NMR ppm: 8.6, 19.6, 20.2, 22.0, 29.2, 29.7, 36.9, 70.8, 118.4, 121.4, 127.5, 145.9, 149.7, 153.8, 169.7, 183.2

Separation of Cyperaquinone and Remirol and Preparation of Methylremirol

After extracting roots and bulbs of *Cyperus nipponicus* with hexane, ethanol was added to the extract. Then, a formed wax component was removed. After concentrating the residue under reduced pressure, hexane was added. The precipitated cyperaquinone was filtered. The filtrate was subjected to column chromatography (Wakogel C-300) on silica gel using a developer (hexane:ethyl acetate=10:1) to obtain remirol. The resulting remirol was methylated in an alkali solution using dimethyl sulfate to obtain methylremirol.

Method for Testing Antifeeding Effect

A test for an antifeeding effect on insects was conducted by the leaf disk method. After wiping off the surface of a leaf of *Ipomoea batatas* with acetone in order to remove extraneous matter on the leaf, a disk having a diameter of 2 cm was cut out with a cork borer, avoiding the veins of the leaf. An acetone solution containing the predetermined amount of samples was applied to the disk, which was sufficiently air-dried. As a control, the same amount of acetone solution was used, and applied to the leaf disk in the same manner as in the sample. Two pieces each of the sample and the control were placed crosswise in a petri dish, and 15 larvae of *Spodoptera litura* FABRICIUS were set in the petri dish to put on the lid. The *Spodoptera litura* FABRICIUS used was the third or fourth instar. This is because the younger the larvae, the greater the effect they receive due to allelochemical. The first or second instar larvae prefer to eat a tender portion of the leaf because they cannot eat hard veins or fiber of the leaf. On the other hand, the fifth or sixth instar larvae move the leafdisk because they are well-built. Further, the antifeeding effect due to allelochemical is lowered because they eat any portion of the leaf. Therefore, it is better not to use the fifth or sixth instar larvae.

The petri dish was allowed to stand in a thermostatic chamber at 25 to 27° C. under light. Two to 5 hours later, 4 pieces of the leaf were taken out to convert them into black and white pictures with a photocopier. Using a scanner, the disk area was digitized, and then the disk area was expressed numerically at the pixel unit on a Mackintosh computer using a free soft NIH image. Then, an antifeedant index was calculated from the ratio of the sample to the control in the amount of pixel to evaluate the test results.

The method of calculating an antifeedant index (AFI) is as follows. First, a standard area of an intact leaf is calculated. The ratio of the area of the leaf consumed by the larvae to the standard area of the leaf was calculated. Then, using the following formula suggested by Alofahi, the antifeedant index was calculated.

Antifeedant index=100×T/(T+C)

In the formula,

T: Total percentage of treated disk consumed

C: Total percentage of control disk consumed

If this index is 30 or less, the tested leaf has antifeeding activity. If it is more than 30, an antifeeding effect is considered to be inactive. When the consumed area of the sample and that of the control is the same, the antifeedant index indicates 50.

Antifeeding Effect

Concerning scabequinone, remirol, cyperaquinone and methylremirol, the AFI and FR were calculated according to the method for testing an antifeeding effect. The results are shown in the following.

TABLE 2

Antifeedant index and consumed ratio of treated leaves

| Compound | | 1 mg/ leaf | 0.25 mg/ leaf | 0.1 mg/ leaf | origin |
|---|---|---|---|---|---|
| scabequinone | AFI | 0 | 2.16 | 4.22 | *Cyperus distans* |
| | FR | 0.47 | 1.61 | | |
| remirol | AFI | 8.57 | 19.02 | 23.45 | *C. nipponicus* |
| | FR | 3.84 | 10.31 | 11.33 | |
| cyperaquinone | AFI | 20.98 | 26.03 | 24.00 | *C. nipponicus* |
| | FR | 9.98 | 13.92 | 16.18 | |
| juglone | AFI | 0 | 0 | 0 | Juglans |
| | FR | 0 | 0 | 0 | (Juglandaceae) |
| quercetin | AFI | 2.07 | 25.08 | 25.04 | buckwheat |
| | FR | 0.66 | 13.07 | 15.96 | acasia |
| methylremirol | AFI | 0 | | | |
| racemic methylremirol | AFI | 44.3 | | | |
| 2-isopopenyl-4,6-methoxy-coumaran | AFI | 26.1 | | | |

As a comparative example, commercially available juglone and quercetin were used.

Evaluation

The antifeeding effect was confirmed in every component. In comparison with the commercially available juglone, scabequinone did quite well in the antifeeding effect, and it was by far superior to another commercially available product quercetin, in the antifeeding effect. The AFI of remirol and cyperaquinone was 30 or less even if they are present in an amount of 0.1 mg/leafdisk, which was proven to be effective.

Antifeeding Effect of Hexane Extracted Cyperaceae Species

Concerning various Cyperaceae species (from Thailand) obtained by the extracting operation described in Example 3, the AFI was determined in the same manner as described above.

TABLE 3

AFI of hexane extracted Cyperaceae species (1 mg/leafdisk)

| Extract | Plant part | AFI ± S.E. |
|---|---|---|
| *Cyperus cyperinus* | whole plant | 53.26 ± 8.10 |
| *C. diffusus* | whole plant | 34.69 ± 1.71 |
| *C. distans* | leaf and stem | 26.03 ± 8.88 |
| | root | 24.40 ± 10.76 |
| *C. iria* | whole plant | 31.58 ± 9.33 |
| *C. javanicus* | whole plant | 28.92 ± 1.72 |
| *C. nutans* | whole plant | 50.92 ± 4.11 |
| *C. pulcherrimus* | whole plant | 41.98 ± 0.82 |
| *C. stoloniferus* | whole plant | 25.15 ± 5.28 |
| *C. trialatus* | whole plant | 47.18 ± 6.57 |

Values shown here are mean ± SE from 3 experiments.

Evaluation

Except for *C. cyperinus*, *C. nutans* and *C. trialatus*, the strong antifeeding effect was shown. They are also proven to be available in the form of an extract.

Test for an Insecticidal Effect

In order to test the insecticidal effect of remirol, methylremirol and scabequinone, acetone was added to each sample and the resulting acetone solution was applied to the third instar larvae of *Plutella maculipennis* CURTIS. Thereafter, Kaiwaredaikon (*Raphanus sativus* LINN, C.V. shijunichi) was fed to them as a feed and the number of survived larvae after 24 hours was counted. $LD_{50}$ (lethal dose 50) was calculated by the probit method.

| Compound | $LD_{50}$ |
|---|---|
| Scabequinone | 1.371 mg |
| Remirol | 0.125 mg |
| Methylremirol | 1.0 mg |

Evaluation

Remirol and methylremirol had a lower $LD_{50}$ than that of scabequinone, and it was found out that remirol and methylremirol were superior to scabequinone in the insecticidal effect.

These active ingredients can be formulated into an insect repellant or a contact insecticide by the conventional preparation method. Namely, the antifeedant and contact insecticide of the present invention may contain necessary vehicles such as a resolvent and diluent, or adjuvants such as solution adjuvants, an emulsifying agent, a suspending agent, a gelling agent, a propellant and a retarder.

Examples of the form of the preparation include emulsions, solutions, hydrates, powders, aerosols and the like, preferably, solutions and hydrates.

The insect repellant and the insecticide of the present invention are generally sprayed.

The concentration of the active ingredients to be used for the preparation is from 1 to 80%, but it is possible to change the concentration depending on the form of the preparation.

EXAMPLES

Example 1

Remirol Emulsion
1) Preparation

| Remirol | 1 part by weight |
|---|---|
| Solpole3005X (manufactured by TOHO KAGAKU KOGYO CO.) | 1 part by weight |
| Xylene | 8 parts by weight |

The above components were mixed to prepare a remirol emulsion.

2) Test

Two sweet potato plants, Narutokintoki (*Ipomea batata* LAM., C.V. kintoki) grown in the field of the department of agriculture of Kinki University wore selected, and the number of leaves thereof was counted beforehand to equalize the number thereof between the two plants. On the other hand, the above-mentioned remirol emulsion was diluted to prepare a 10% aqueous solution. The aqueous solution (200 ml, the amount of active ingredient: about 2 g) was sprayed on the plants to give a treated area i.e., an area treated by the preparation. After treatment, the treated area and the untreated area were surrounded by the same cage, and 10 larvae in total of male and female *Spodoptera litura* FABRICIUS were set in the cage. Three weeks later, the consumed ratio and the number of insects were counted. From the number of insects in the treated area relative to that in the untreated area, the insect repelling ratio was calculated. Concerning the consumed ratio, it was visually assayed by any eaten trace on the leaves. Further, growth efficiency of the plants was expressed by the ratio of fresh weight in the above-ground part to that of the control.

3) Results

|  | insect repelling ratio (%) | consumed ratio | growth efficiency of plant (%) |
|---|---|---|---|
| Treated area | 53% | + | 127% |
| Untreated area | 0% | +++ | 100% |

The consumed ratio to one leaf:
+++: more than 50%; ++: more than 30%, +: more than 10%

4) Evaluation

From the results, when we left the choice to the insects, it was observed that the insects tended to move to the untreated area. It was suggested that the preparation of the present invention produced a mild insect repelling effect and therefore could protect crops.

Example 2

Scabequinone Emulsion
1) Preparation

| Scabequinone | 1 part by weight |
|---|---|
| Solpole3005X | 1 part by weight |
| Xylene | 8 parts by weight |

The above-mentioned components were mixed to prepare a scabequinone emulsifiable concentrate.

2) Test

Two sweet potato plants Narutokintoki (i Ipomea batataLAM., C.V. kintoki) grown in the field of the department of agriculture of Kinki University were selected, and the number of leaves thereof was counted beforehand to equalize the number thereof between the two plants. On the other hand, the above-mentioned remirol emulsion was diluted to prepare a 10% aqueous solution. The aqueous solution (200 ml, the amount of active ingredient: about 2 g) was sprayed on the plants to give an area treated by the preparation. After treatment, the treated area and the untreated area were surrounded by the same cage, and 10 larvae of *Spodoptera litura* FABRICIUS were set in the cage. Three weeks later, the consumed ratio and the number of insects were counted. From the number of insects in the treated area relative to that in the untreated area, the insect repelling ratio was calculated. Concerning the consumed ratio, it was visually assayed by whether there is any eaten trace on the leaves. Further, growth efficiency of the plants was expressed by the ratio of fresh weight in the above-ground part to that of the control.

3) Results

|  | insect repelling ratio (%) | consumed ratio | growth efficiency of plant (%) |
|---|---|---|---|
| Treated area | 70% | — | 180% |
| Untreated area | 0% | +++ | 100% |

The consumed ratio to one leaf:
+++: more than 50%; ++: more than 30%; +: more than 10%; and −1: less than 10%.

4) Evaluation

From the above-mentioned results, when we left the choice to the insects, it was observed that the insects tended to move to the untreated area. It was suggested that the preparation of the present invention produced a strong insect repelling effect, and as the result, could protect crops.

Example 3
Preparation of Hexane Extract of Cyperaceae Species
1) Preparation Dried *Cyperus distans* collected in Thailand (100 g) was soaked in 200 ml of hexane at 4° C. for about 72 hours (3 days), followed by filtration. The filtrate was concentrated under reduced pressure to obtain about 1 g of a crude extract. The obtained extract was suspended in an aqueous solution containing a 10% surface active agent (TWEEN20), and then 20 mg of a spreading agent (DINE) was added thereto to prepare a hexane extract.

2) Test

The insect repellant effect on sweet potato by an extract of Cyperaceas species was evaluated. Two sweet potato plants Narutokintoki (*Ipomea batata* LAM., C.V. kintoki) grown in the field of the department of agriculture of Kinki University were selected, and the number of leaves thereof was counted beforehand to equalize the number thereof between the two plants. The repellant was sufficiently sprayed on the sweet potato plant in the treated area, while the repellant was never sprayed in the untreated area. After treatment, the treated area and the untreated area were surrounded by the same cage, and 10 larvae of *Spodoptera litura* FABRICIUS were set in the cage. Three weeks later, the consumed ratio and the number of insects were counted. From the number of insects in the treated area relative to that in the untreated area, the insect repelling ratio was calculated. Concerning the consumed ratio, it was visually assayed by whether there is any eaten trace on the leaves. Further, growth efficiency of the plants was expressed by the ratio of fresh weight in the above-ground part to that of the control.

3) Results

|  | insect repelling ratio (%) | consumed ratio | growth efficiency of plant (%) |
|---|---|---|---|
| Treated area | 60% | + | 115% |
| Untreated area | 0% | +++ | 100% |

The consumed ratio to one leaf:
+++: more than 50%; ++: more than 30%; +: more than 10% and −: less than 10%

4) Evaluation

From the above-mentioned results, when we left the choice to the insects, it was observed that the insects tended to move to the untreated area. It was suggested that the preparation of the present invention produced a strong insect repelling effect, as the result, could protect crops.

Example 4
Preparation of Hexane Extract of Cyperaceae Species
1) Preparation An extracted preparation was prepared in the same manner as in Example 3.

2) Test

It was conducted in the same manner as in Example 3, except that a seedling of cabbage was used instead of a sweet potato plant.

3) Results

|  | insect repelling ratio (%) | consumed ratio | growth efficiency of plant (%) |
|---|---|---|---|
| Treated area | 60% | + | 115% |
| Untreated area | 0% | +++ | 100% |

The consumed ratio to one leaf:
+++: more than 50%; ++: more than 30%; +: more than 10%; and −: less than 10%

4) Evaluation

From the above-mentioned results, when we left the choice to the insects, it was observed that the insects tended to move to the untreated area. It was suggested that the preparation of the present invention produced a strong insect repelling effect and, as a result, could protect crops.

Example 5
1) Test

To 1 mg of cyperaquinone was added acetone and the resulting solution was charged in a test tube (a diameter of 1 cm). Thereafter, the solution was treated by the dry film method. (The method is as follows: a solution was charged at the bottom of a test tube. After applying the solution to the wall of the test tube, the solvent was removed to leave a sample on the wall of the test tube.) Fifty *Tyrophagus putrescentiae* SCHRANK were set in the test tube. After growing them at 25° C. for 1 day, the confirmation was conducted with a stereomicroscope.

2) Evaluation

It was confirmed that some of the *Tyrophagus putrescentiae* SCHRANK fled upward avoiding the applied part and therefore cyperaquinone had a repelling effect on *Tyrophagus putrescentiae* SCHRANK. Some of the *Tyrophagus putrescentiae* SCHRANK were dead and gathered at the bottom of the test tube.

What is claimed is:

1. A method of protecting crop plants from harmful insects which comprises preventing said insects from feeding on the crop plants by applying to the plants an antifeedant comprising as an active ingredient an effective amount of at least one compound selected from the group consisting of scabequinone, remirol cyperaquinone, dihydroscabequinone, 2-isopentyl-3-methoxy-4,5-franobenzoquinone, 2-isopentenyl-3-methoxy-4,5-franobenzoquinone, 2-isopropenyl-4,6-dimethoxycoumaran, methylremirol, epoxyremirol, acetyl remirol, and $C_{1-6}$-alkylsubstituted-remirol.

* * * * *